US005558879A

United States Patent [19]

Chen et al.

[11] Patent Number: 5,558,879
[45] Date of Patent: Sep. 24, 1996

[54] CONTROLLED RELEASE FORMULATION FOR WATER SOLUBLE DRUGS IN WHICH A PASSAGEWAY IS FORMED IN SITU

[75] Inventors: Chih-Ming Chen, Cooper City; Der-Yang Lee, Plantation, both of Fla.

[73] Assignee: Andrx Pharmaceuticals, Inc., Fort Lauderdale, Fla.

[21] Appl. No.: 431,404

[22] Filed: Apr. 28, 1995

[51] Int. Cl.⁶ .............................. A61K 9/22; A61K 9/24; A61K 9/36
[52] U.S. Cl. .................. 424/480; 424/465; 424/468; 424/472; 424/473; 514/781; 514/853; 514/960
[58] Field of Search ........................... 424/472, 473, 424/480, 465, 468

[56] References Cited

U.S. PATENT DOCUMENTS

| | | | |
|---|---|---|---|
| 3,065,143 | 11/1962 | Christenson et al. | 167/82 |
| 3,845,770 | 11/1974 | Theeuwes et al. | 128/260 |
| 3,916,899 | 11/1975 | Theeuwes et al. | 128/260 |
| 4,016,880 | 4/1977 | Theeues et al. | 128/260 |
| 4,285,987 | 8/1981 | Ayer et al. | 427/3 |
| 4,369,172 | 1/1983 | Schor | 424/19 |
| 4,389,393 | 6/1983 | Schor | 424/19 |
| 4,704,285 | 11/1987 | Alderman | 424/468 |
| 4,783,337 | 11/1988 | Wong et al. | 424/468 |
| 4,801,461 | 1/1989 | Hamel | 424/467 |
| 5,019,396 | 5/1991 | Ayer et al. | 424/473 |

OTHER PUBLICATIONS

Shin Etsu Bulletin, Jan. 1993.
Dow Technical Information Bulletin, Feb. 1991.

*Primary Examiner*—James M. Spear
*Attorney, Agent, or Firm*—Hedman, Gibson, & Costigan, P.C.

[57] ABSTRACT

A controlled release pharmaceutical tablet is disclosed which is based on:

(a) a compressed core which contains:
  (i) a medicament;
  (ii) from 5 to 20% by weight of a water soluble osmotic agent based on the total weight of the compressed core;
  (iii) a water soluble pharmaceutically acceptable polymeric binder;
  (iv) a conventional pharmaceutical excipient; and
(b) a dual layer membrane coating around said core which consists essentially of:
  (i) a first inner coating layer for sustained release of the medicament, said inner coating layer consisting essentially of a plasticized water insoluble pharmaceutically acceptable polymer and a pharmaceutically acceptable water soluble polymer, and;
  (ii) a second outer coating layer for immediate release of a medicament, said outer coating layer consisting essentially of an effective amount of a medicament and a water soluble polymer.

The controlled release formulation is suitable for the once-a-day administration of medicaments.

10 Claims, 6 Drawing Sheets

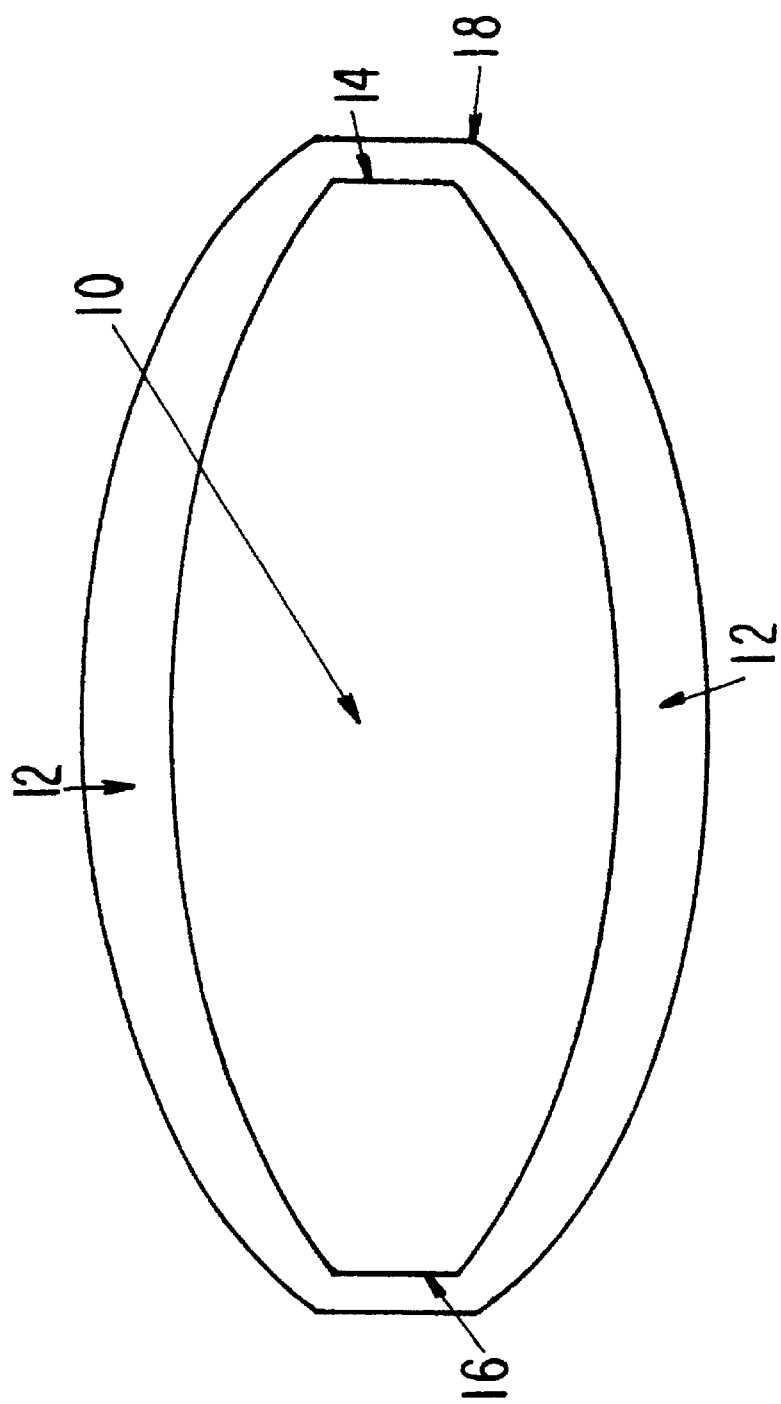

CONTROLLED RELEASE FORMULATION FOR WATER SOLUBLE DRUGS IN WHICH A PASSAGEWAY IS FORMED IN SITU

BACKGROUND OF THE INVENTION

The present invention relates to controlled release unit dose formulations of pharmaceuticals. In the prior art many techniques have been used to provide controlled and extended release pharmaceutical dosage forms in order to maintain therapeutic serum levels of medicaments and to minimize the effects of missed doses of drugs caused by a lack of patient compliance.

In the prior art extended release tablets containing osmotic tablets containing water insoluble drugs have been described which have had an osmotically active drug core surrounded by a semipermeable membrane. The core is divided into two layers one of which contains the active drug and the other contains a push layer of pharmacologically inactive ingredients which are osmotically active in the presence of gastrointestinal fluids. An outer water impermeable coating covers the tablet which is provided with an aperture that is formed by laser drilled orifice to allow gastrointestinal fluids to reach the osmotic push layer to activate the tablet and to begin to push out the active medicament. A product of this type is disclosed in U.S. Pat. No. 4,783,337 and is sold commercially as Procardia XL®.

The osmotic dosage forms that are disclosed in U.S. Pat. No. 4,783,337 are described as having a passageway which includes an aperture, orifice, hole, porous element, hollow fiber, capillary tube, microporous insert, pore, microporous overlay or bore which extends through the semipermeable lamina, the microporous lamina, or through the laminated wall. The patent also states that the passageway may be formed by mechanical drilling, laser drilling, eroding an erodible element, extracting, dissolving, bursting or leaching a passageway-former from the wall of the osmotic dosage form (col. 14, line 35 et seq.) which are implicitly pre-formed in the tablet during the manufacturing process. The only exemplified technique of forming a passageway in U.S. Pat. No. 4,783,337 is the use of a laser to drill a hole in the outer layer of the tablet.

U.S. Pat. No. 4,285,987 described an osmotic tablet which had a laser drilled aperture into the core of the tablet. The laser drilled hole was plugged with leachable sorbitol which was leached out in the presence of gastrointestinal fluid.

U.S. Pat. No. 3,845,770 discloses an osmotic dispensing device for soluble drugs or soluble derivatives of drugs. That device has an external membrane, a compartment with a soluble active agent and an osmotic agent and an osmotic passageway which allows external fluid to be continuously imbibed.

U.S. Pat. No. 4,801,461 discloses a dosage form which provides for the controlled release of pseudoephedrine over an extended period of time. The dosage form contains an osmagent such as sodium chloride and hydroxypropyl methyl cellulose and is provided with a passageway.

U.S. Pat. No. 4,016,880 describes an osmotic tablet which has one or more openings in the side wall which are formed in situ and allow gastrointestinal fluids to have access to the core of the tablet.

The present invention is concerned with providing an osmotic tablet that is designed to provide once a day dosing of water soluble drugs but does not have a pre-formed osmotic passageway. In addition the osmotic tablet of the invention is designed to avoid the need to have a separate "push" layer in the core which contains no medicament and which avoids the need to have a pre-formed passageway or a leachable plug in the tablet to allow the gastrointestinal fluid to reach the osmotic core.

SUMMARY OF THE INVENTION

The present invention is directed to a controlled release pharmaceutical tablet which comprises:
(a) a compressed core which consists essentially of
  (i) a medicament;
  (ii) from 5 to 20% by weight of a water soluble osmotic agent;
  (iii) a water soluble pharmaceutically acceptable polymeric binder;
  (iv) a conventional pharmaceutical excipient; and
(b) a dual layer membrane coating around said core which consists essentially of:
  (i) a first inner coating layer for sustained release of the medicament, said inner coating layer consisting essentially of a plasticized water insoluble pharmaceutically acceptable polymer and a pharmaceutically acceptable water soluble polymer, and;
  (ii) a second outer coating layer for immediate release of a medicament, said outer coating layer consisting essentially of an effective amount of a medicament and a water soluble polymer.

It is an object of the invention to provide a a controlled release pharmaceutical tablet for water soluble drugs which has an osmotic core covered with a external polymeric membrane that provides therapeutic blood levels with once a day administration.

It is also an object of the present invention to provide a controlled release pharmaceutical tablet that has an osmotic core and no pre-formed aperture in the external polymeric membrane.

It is also an object of this invention to provide a controlled release pharmaceutical tablet having a single component osmotic core wherein the core component may be made using ordinary tablet compression techniques.

These and other objects of the invention will become apparent from the appended specification.

BRIEF DESCRIPTION OF THE DRAWINGS

FIG. 3 is a cross-section of a tablet of the invention which shows the opening through a portion of the edge of the tablet which is observed within two hours after a tablet is placed in an aqueous fluid.

DETAILED DESCRIPTION OF THE INVENTION

Figure 1:
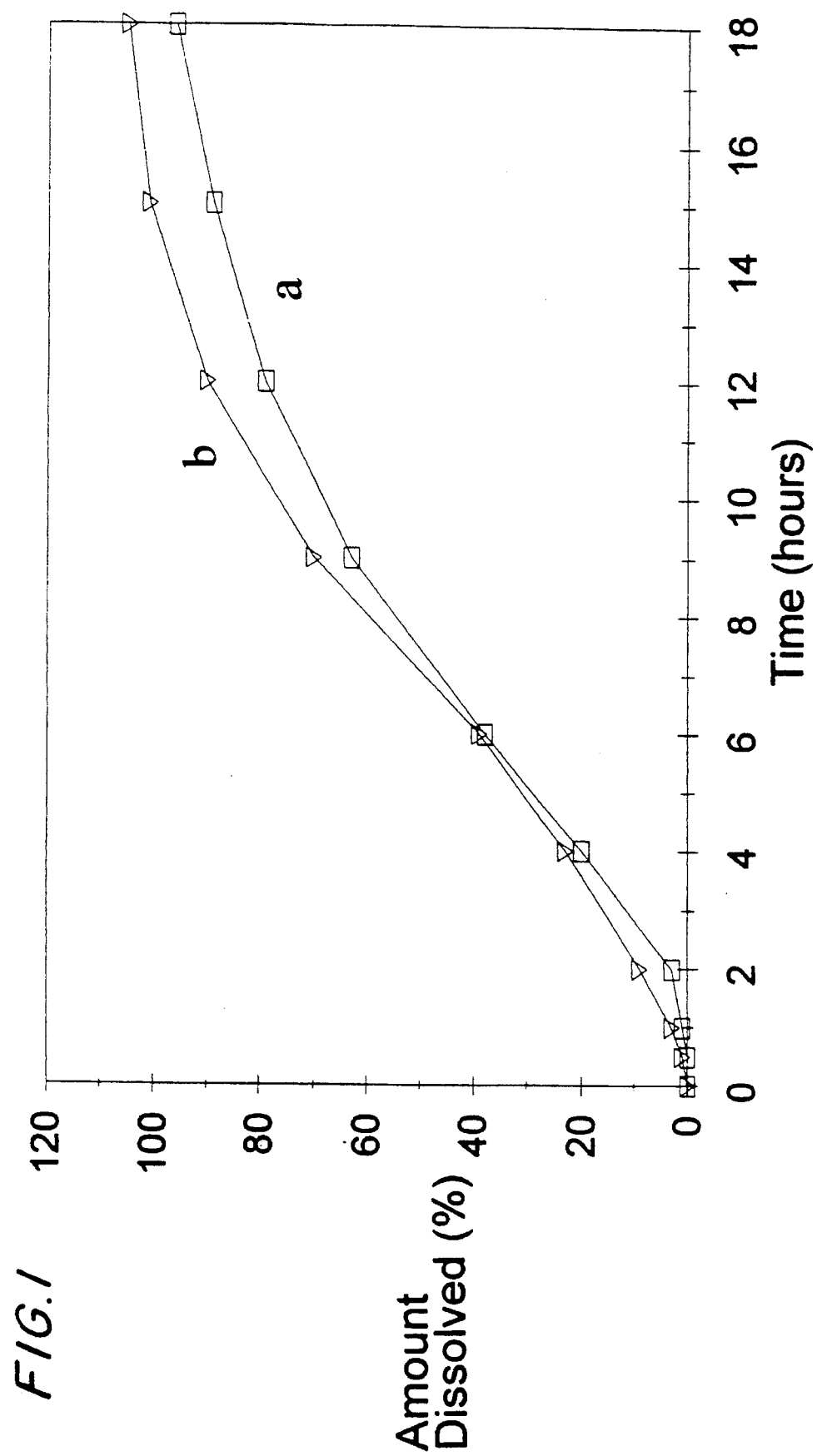
FIG. 1 is a graph of in vitro dissolution data which compares the amount of pseudoephedrine HCl released in water in a USP Type II dissolution apparatus at 100 rpm from a sustained release coated core tablet having no immediate release layer which is otherwise prepared according to the invention and contains 180 mg of pseudoephedrine HCl and a modified Efidac®/24.

The controlled release osmotic tablet formulation of the invention provides performance which is equivalent to much more complicated prior art controlled release dosage formulations which require a complex segmented osmotic core and a pre-formed osmotic aperture in the external membrane which is applied around the osmotic core.

The core of the controlled release tablet of the present invention is made by initially forming granules by combining a medicament and a water soluble osmotic agent with conventional excipients and a water soluble polymeric binder. Thereafter, the granules are blended with suitable excipients to form a composition which may be compressed into tablets. A tabletting machine is used to compress the mixture of granules into a tablet core which is subsequently coated with a water insoluble polymeric membrane to form the controlled release tablet of the invention.

Although the inventor does not wish to be bound by any theory by which the present invention operates, it is believed that the use of the plasticizer in combination with the water insoluble polymer to form the external membrane around the core of the tablet, results in a membrane which will allow water to be imbibed into the core of the tablet even in the absence of a preformed aperture. As water is taken up into the core of the tablet, the medicament and the water soluble osmotic agent dissolve which causes an increase in the osmotic pressure inside the tablet. This causes a small opening to form at the weakest point in the membrane which is at the edge of the tablet. Once the initial opening is formed at a single point, the osmotic effect of the core components in commences to extrude the contents of the core through the initial opening. The internal pressure which is exerted on the membrane by the osmotic core is relieved by the passage of the first portion of the core contents through the initial opening and no other opening is observed. This effect is illustrated in FIG. 3 and is unexpected because it could not have been predicted that only a single opening in the membrane would occur rather than a bursting of the membrane. Based on observation, it is believed that the formation of the single opening without loss of the integrity of the rest of the membrane by the action of the osmotic core is responsible for the 24 hour therapeutic blood level which may be achieved by the controlled release tablet of the invention. An outer immediate release layer is provided which contains an amount of medicament which is approximately equivalent to a single dose of the particular medicament which is dissolved in a water soluble binder.

FIG. 3 shows a cross-section of a tablet of the invention which illustrates the internal structure of the tablet with core element 10 and membrane 12. The relatively thin membrane at edges 14 and 16 is shown by the cross-section. The extruding portion of the core is hardly observed after the tablet is placed in an aqueous fluid since the medicament and osmotic agent are very soluble in water.

Figure 4A:
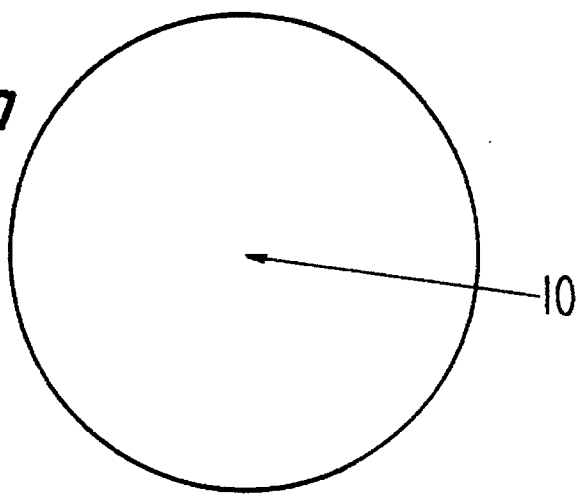
FIG. 4a is a top view of a tablet according to the invention before it is placed in a USP Type II dissolution apparatus.
Figure 4B:
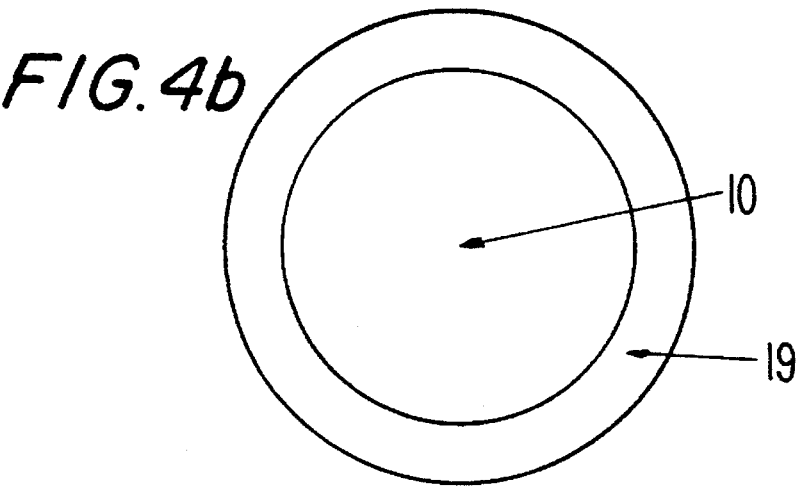
FIG. 4b is a top view of a tablet according to the invention about 2–3 hours after it is placed in a USP Type II dissolution apparatus.
Figure 4C:
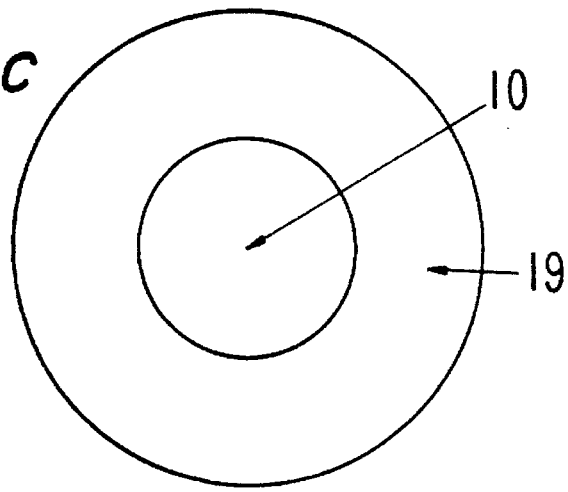
FIG. 4c is a top view of a tablet according to the invention about 14 hours after it is placed in a USP II Type II dissolution apparatus.
Figure 5:
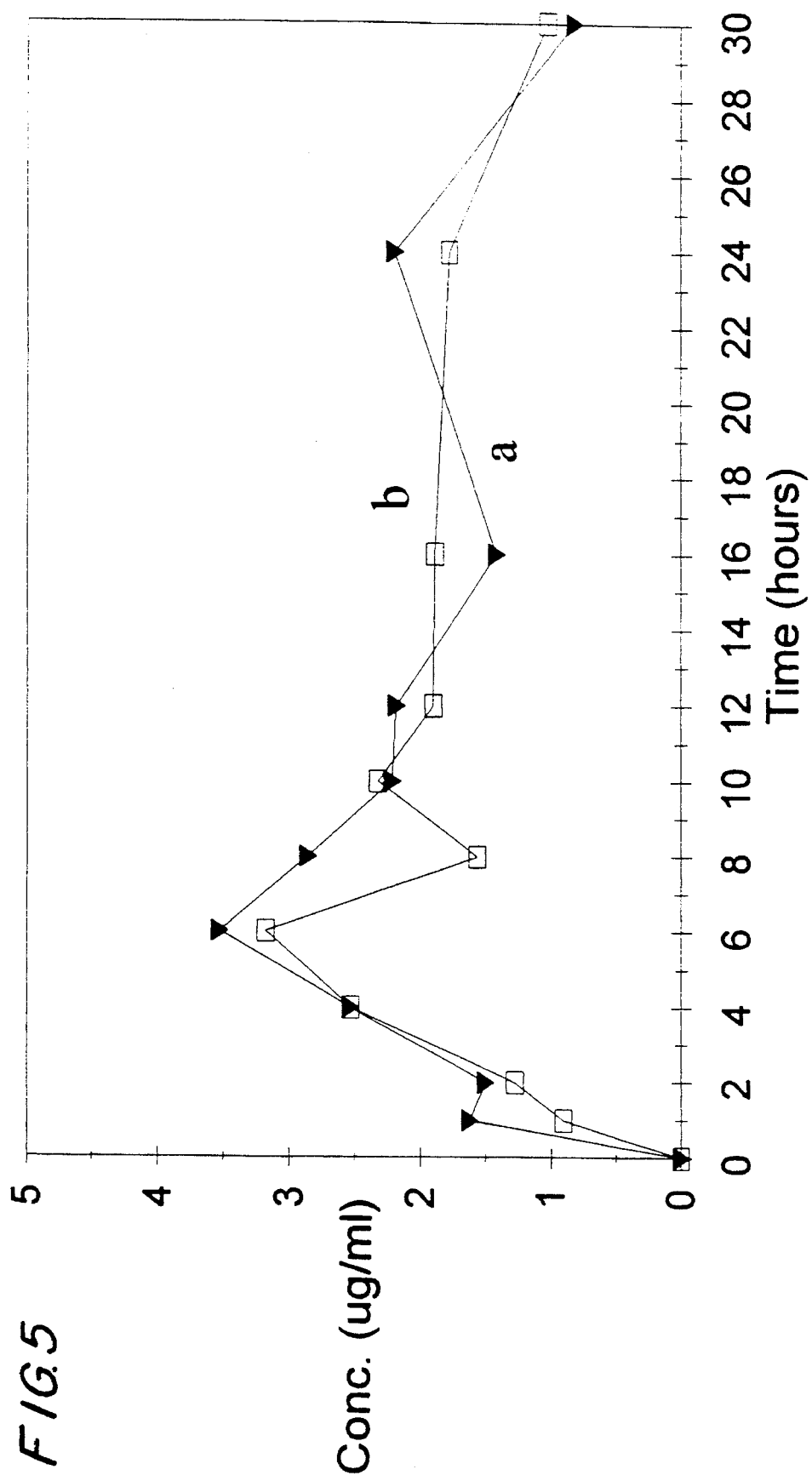
FIG. 5 is a graph which compares the mean plasma concentration of Efidac®/24 (b) and the pseudoephedrine hydrochloride tablet (a) whose dissolution profile is shown in FIG. 2. This data was obtained in a crossover study of 6 human volunteers who were fasting.
Figure 6:
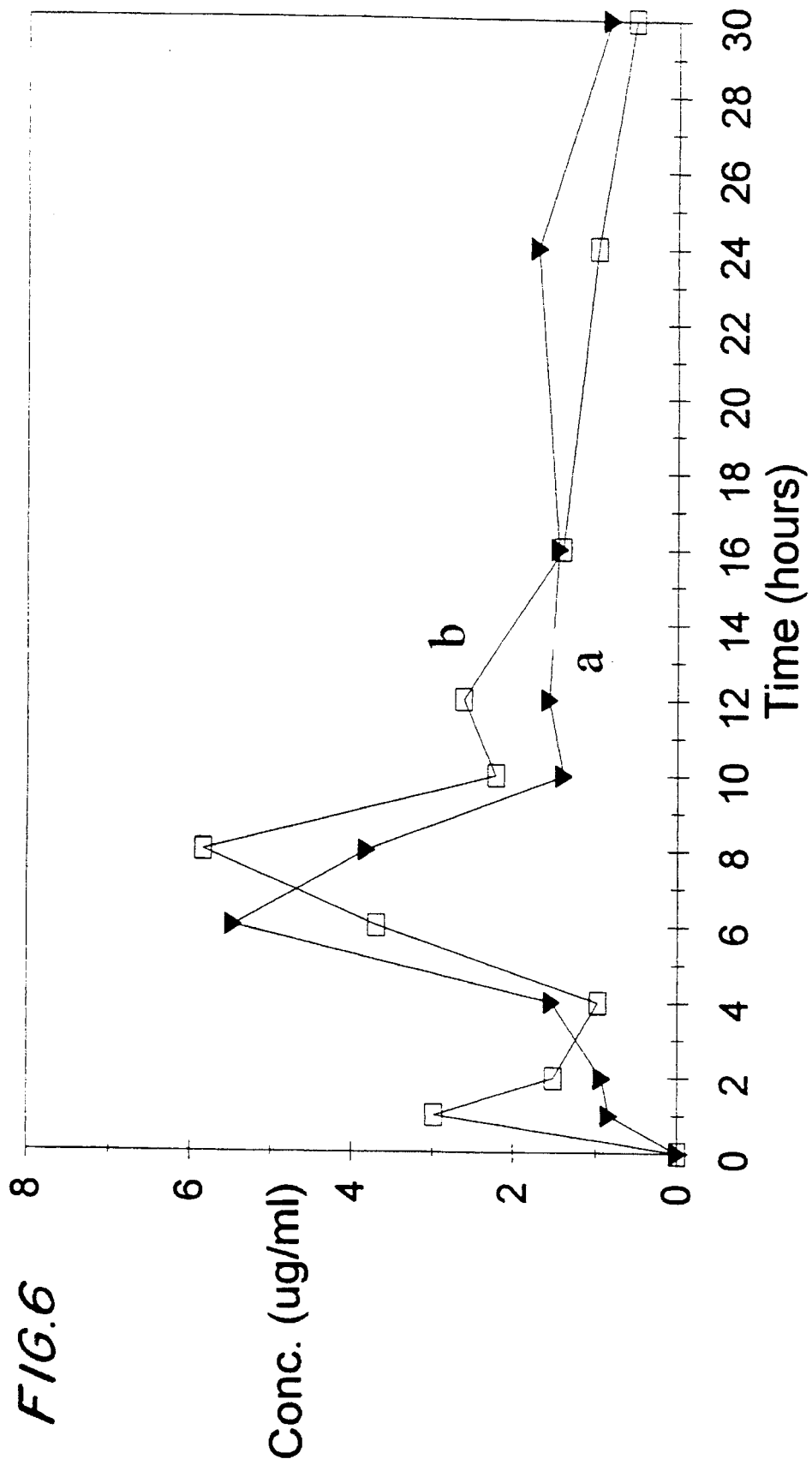
FIG. 6 is a graph which compares the mean plasma concentration of Efidac®/24 (b) and the pseudoephedrine hydrochloride tablet (a) whose dissolution profile is shown in FIG. 2. This data was obtained in a crossover study of 6 human volunteers who were fed.

FIGS. 4a–4c are top views of the tablet of the invention which show the changes that are observed over a period of 18 hours when the tablet is placed in a aqueous fluid. The core contents start to diffuse out of the tablet once the initial opening 18 is formed. Subsequently, a zone 19 is observed which is the core that is observed through a peripheral zone 19 of the tablet coating which becomes translucent when placed in an aqueous fluid. A comparison of FIG. 4b and FIG. 4c shows that the core section 10 becomes smaller over time while the peripheral zone 19 becomes larger.

The controlled release tablet of the invention is primarily intended to be used to administer medicaments which are water soluble. (e.g. 1 part of drug dissolves in 5 parts of water or less).

Various therapeutic types of medicaments may be employed such as decongestants, antihistamines, analgesics, sedatives, anti-inflammatory, anti-depressants, antihypertensives and the like at therapeutic dosage levels.

Examples of specific medicaments which may be utilized, at therapeutic dose levels, in the controlled release tablets of the invention include ephedrine, pseudoephedrine, phenylpropanolamine, chlorpheniramine, diphenhydramine, dimenhydramine, indomethacin, labetalol, albuterol, haloperidol, amitriptyline, clofenac, clonidine, terfenadine, fentanyl, and the like which are in the form of a water soluble salt such as the hydrochloride or sodium salt or in the from of an ester, ether, amide, complex or the like.

The water soluble osmotic agent is any non-toxic pharmaceutically acceptable compound which will dissolve sufficiently in water and increase the osmotic pressure inside of the core of the tablet. The amount of the osmotic agent may be from about 5 to 20 wt % and preferably from about 8 to 15 wt % based on the total weight of the compressed core. These osmotic agents include sodium chloride, potassium chloride, magnesium sulfate, magnesium chloride, sodium sulfate, lithium sulfate, urea, inositol, sucrose, lactose, glucose, sorbitol, fructose, mannitol, dextrose, magnesium succinate, potassium acid phosphate and the like.

The water soluble binder may be any pharmaceutically acceptable film former which can be utilized to bind the powder mixture together with an adhesive instead of compaction in order to form granules for making compressed tablets. These polymers include polyvinyl pyrrolidone, carboxyvinyl polymer, methylcellulose, hydroxyethylcellulose, hydroxypropylcellulose, hydroxypropylmethylcellulose, dextrin, maltodextrin, and the like. These materials are formed into a dispersion or solution in water or other solvent system at a sufficient concentration to have a binding effect on the osmotic agent, the medicament and any excipient. This will generally require a concentration of about of 5 to 15 wt % of the film former.

Generally the binder is used in a sufficient amount so that when it is combined with a suitable solvent, combined with the water soluble osmotic agent and agitated, granules will be formed which may be compressed into a tablet core. Prior to compressing the granules, conventional pharmaceutical excipients such as microcrystalline cellulose, lactose, dextrose and the like may be added to the granule forming mixture in amounts of from about 5 to 20 wt % based on the weight of the compressed core.

The membrane coating around said core consists essentially of a plasticized water insoluble pharmaceutically acceptable polymer. Suitable water insoluble polymers include cellulose esters, cellulose ethers and cellulose ester-ethers. The cellulosic polymers have a degree of substitution greater than 0 up to 3. The degree of substitution is calculated as the average number of original hydroxyl groups on the anhydroglucose unit which makes up the cellulose polymer which are replaced with a substitute group. These materials include cellulose acylate, cellulose ethyl ether, cellulose diacylate, cellulose triacylate, cellulose acetate, cellulose diacetate, cellulose triacetate, mono-, di- and tri-cellulose alkan, mono-, di- and tricellulose aroyl and the like. Ethylcellulose is the preferred polymer. Other water insoluble polymers are disclosed in U.S. Pat. No. 4,765,989 which is incorporated by reference. If desired other cellulosic polymers may be combined with the water insoluble polymer to modify the permeability of the membrane coating around the core. These include hydroxymethyl cellulose, hydroxypropyl cellulose or cellulose per se. Generally, the sustained release coating will comprise from about 3 to 7.5 wt % based on the total weight of the core tablet.

The water insoluble polymer may be plasticized with a plasticizing amount of a plasticizer. The preferred plasticizer is triacetin but materials such as acetylated monoglyceride, rape oil, olive oil, sesame oil, acetyltributylcitrate, acetyltriethylcitrate, glycerin sorbitol, diethyloxalate, diethylmalate, diethylfumarate, dibutylsuccinate, diethylmalonate, dioctylphthalate, dibutylsebacate, triethylcitrate, tributylcitrate, glyceroltributyrate, polyethyleneglycol having a molecular weight of from 380 to 440, propylene glycol and mixtures thereof. Depending on the particular plasticizer, the amount of the plasticizer may be from 1% to 25%, and preferably from 10 to 20% by weight of the total weight of the plasticizer, the water soluble polymer and the water insoluble polymer, may be utilized.

In the preparation of the tablets of the invention, various solvents may be used to prepare the granules and apply the external coating to the tablets of the invention. In addition, various diluents, excipients, lubricants, dyes, pigments, dispersants etc. may be used to optimize the formulations of the invention.

DESCRIPTION OF THE PREFERRED EMBODIMENTS

EXAMPLE

A tablet having the following formula was prepared:

I Granulation

| | |
|---|---|
| psuedoephedrine HCl | 74.80 wt % |
| microcrystalline cellulose, NF | 10.27 wt % |
| sodium chloride, USP powder | 9.73 wt % |
| povidone[1], USP | 5.20 wt % |
| purified water* | (10 times the amount of povidone) |

[1]weight average molecular weight = 55,000; freely soluble in water (1 g in 1–10 ml of water); dynamic viscosity (10% w/v solution at 20° C.) = 5.5–8.5 m Pa s
*water is evaporated during the granulation process.

(a) The povidone is slowly dispersed in water to make a 10 wt. % solution. Then the pseudoephedrine hydrochloride, sodium chloride and microcrystalline cellulose are mixed and placed in a fluidized-bed dryer and the povidone solution is sprayed onto the mixture to form granules. The drying cycle is initiated after the granulation process is completed. The drying cycle is continued until the moisture loss on drying (LOD) is not more than 2.0% at about 50° C. Then, the dry granules are sized with a 40 mesh (USS) screen in an oscillating granulator.

II Tabletting

| | |
|---|---|
| granules (from I) | 96.24 wt % |
| hydroxypropyl methylcellulose (Methocel K-100 M)[2] | 2.96 wt % |
| magnesium stearate | 0.8 wt % |

[2]Weight average mol. wt. 246,000

(b) A tablet core is made by adding 2.96 wt % of hydroxypropyl methylcellulose and 0.8 wt % of magnesium stearate to 96.24 wt % of the granules prepared in step (a). Core tablets weighing 250 mg each are prepared using a tablet press machine using a 0.3750" standard concave punches and die.

III Sustained Release Coating

| | |
|---|---|
| ethylcellulose[3] | 58.5 wt % |
| hydroxypropyl cellulose, NF (Klucel ® EF)[4] | 29.2 wt % |
| triacetin | 12.3 wt % |
| acetone* | (17 × the amount coating materials) |

[3]ethoxy content = 48.0 to 49.5%; number average molecular weight = 10,500; solution viscosity (5% w/v in 80% toluene and 20% ethanol at 25° C. in an Ubbelohde viscometer) = 9 to 11 centipoises.
[4]Klucel ® EF, NF; viscosity 200–600 cps; (10% soln. H2O, 25° C.) Mwn = 80,000; hydroxy/propyl ratio = 3.4–4.4
Particle size; 20 and above mesh = 0 wt % retained; 30 and above mesh size = 2.2 wt % retained; total through 30 mesh 97.8 wt %
*acetone is evaporated during the granulation process.

(c) The core tablet of step (b) is provided with a sustained release coating that is applied with a coating solution (III). The coating is applied using a fluid bed coater until the tablets show a weight gain of 5.4%.

IV Immediate release coating

| | |
|---|---|
| pseudoephedrine HCl | 81.1 wt % |
| hydroxypropyl cellulose, NF (Klucel ® EF | 13.5 wt % |
| polysorbate 80 | 5.4 wt % |
| water* | (the weight of water is equal to the weight of the tablets) |

*water is evaporated during the coating process.

(d) An immediate release coating is applied to the tablets prepared in step (c) by coating the tablets with an immediate release coating solution (IV). The coating is applied using a fluid bed coater or a perforated coating pan until the tablets exhibit a weight gain of 19.8%.

Several of the coated tablets were placed in a Type II, USP dissolution apparatus having 900 ml of purified water at 37.2° C. which is stirred at 100 rpm with a paddle. After about two hours, a single aperture forms in the edge of the side of the tablet as shown in FIG. 3 and the core contents begin to extrude out of the coated tablet.

Figure 2:
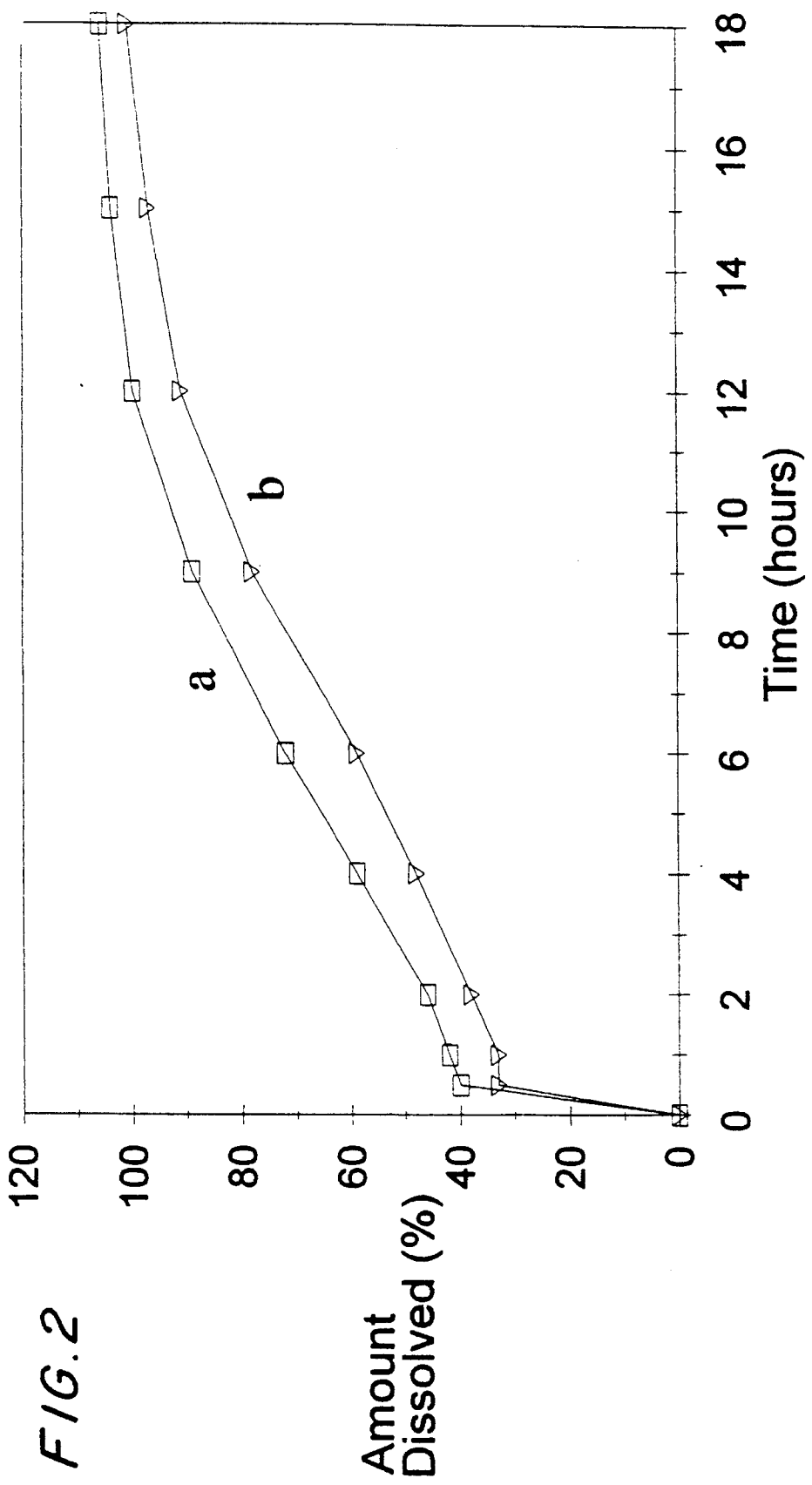
FIG. 2 is a graph of the in vitro dissolution data which compares the amount of pseudoephedrine HCl released in water in a USP Type II dissolution apparatus at 100 rpm from a 240 mg tablet prepared according to the invention and Efidac®/24.

The data of FIG. 1 compares a core tablet, prepared according to the present invention except that no immediate release layer is present with an Efidac®/24 tablet that has been modified by washing in deionized water at room temperature to remove the immediate release coating. FIG. 2 compares a tablet prepared according to the present invention which has an immediate release layer with unmodified Efidac®/24.

While certain preferred and alternative embodiments of the invention have been set forth for purposes of disclosing the invention, modifications to the disclosed embodiments may occur to those who are skilled in the art. Accordingly, the appended claims are intended to cover all embodiments of the invention and modifications thereof which do not depart from the spirit and scope of the invention.

I claim:

1. A controlled release pharmaceutical tablet which consists essentially of:
   (a) a compressed core which consists essentially of
      (i) a medicament;
      (ii) from 5 to 20% by weight of a water soluble osmotic agent based on the total weight of the compressed core;
      (iii) a water soluble pharmaceutically acceptable polymer binder;
      (iv) a conventional pharmaceutical excipient; and
   (b) a dual layer membrane coating around said core which consists essentially of:
      (i) a first inner coating layer for sustained release of the medicament, said inner coating layer consisting essentially of a plasticized water insoluble pharmaceutically acceptable polymer and a pharmaceutically acceptable water soluble polymer, and;
      (ii) a second outer coating layer for immediate release of a medicament, said outer coating layer consisting essentially of an effective amount of a medicament and a water soluble polymer.

2. A controlled release pharmaceutical tablet as defined in claim 1 wherein the medicament is selected from the group consisting of ephedrine, pseudoephedrine, phenylpropanolamine, chlorpheniramine, diphenhydramine, dimenhydramine, indomethacin, labetalol, albuterol, haloperidol, amitriptyline, clofenac, clonidine, terfenadine and fentanyl which are in the form of a water soluble salt or in the form of a water soluble ester, ether, amide or complex.

3. A controlled release pharmaceutical tablet as defined in claim 1 wherein the water soluble osmotic agent is selected from the group consisting of sodium chloride, potassium chloride, magnesium sulfate, magnesium chloride, sodium sulfate, lithium sulfate, urea, inositol, sucrose, lactose, glucose, sorbitol, fructose, mannitol, dextrose, magnesium succinate, potassium acid phosphate and mixtures thereof.

4. A controlled release pharmaceutical tablet as defined in claim 1 wherein the polymer binder is polyvinyl pyrrolidone.

5. A controlled release pharmaceutical tablet which comprises:
   (a) a compressed core which consists essentially of
      (i) a medicament;
      (ii) from 5 to 20% by weight of a water soluble osmotic agent based on the total weight of the compressed core;
      (iii) a water soluble pharmaceutically acceptable polymer binder;
      (iv) a conventional pharmaceutical excipient; and
   (b) a dual layer membrane coating around said core which consists essentially of:
      (i) a first inner coating layer for sustained release of the medicament, said inner coating layer consisting essentially of a plasticized water insoluble pharmaceutically acceptable polymer and a pharmaceutically acceptable water soluble polymer, and;
      (ii) a second outer coating layer for immediate release of a medicament, said outer coating layer consisting essentially of an effective amount of a medicament and a water soluble polymer wherein the water insoluble polymer in the membrane around the core is plasticized with triacetin.

6. A controlled release pharmaceutical tablet as defined in claim 1 wherein the water insoluble polymer in the membrane around the core is a water insoluble cellulosic polymer.

7. A controlled release pharmaceutical tablet as defined in claim 6 wherein the water insoluble cellulosic polymer in the membrane around the core is ethyl cellulose.

8. A controlled release pharmaceutical tablet as defined in claim 7 wherein the membrane around the core includes hydroxypropyl cellulose.

9. A controlled release pharmaceutical tablet which comprises:
   (a) a compressed core which consists essentially of
      (i) a decongestant and/or an antihistamine;
      (ii) from 5 to 20% by weight of a water soluble osmotic agent based on the total weight of the compressed core;
      (iii) a water soluble pharmaceutically acceptable polymer binder;
      (iv) a conventional pharmaceutical excipient; and
   (b) a dual membrane coating around said core which consists essentially of:
      (i) an inner membrane of triacetin plasticized ethyl cellulose and hydroxypropylcellulose; and
      (ii) an outer membrane of pseudoephedrine and terfenadine and hydroxypropyl cellulose.

10. A controlled release pharmaceutical tablet which comprises:
    (a) a compressed core which consists essentially of:
       (i) pseudoephedrine hydrochloride and terfenadine, and
       (ii) from 5 to 20% by weight of a water soluble osmotic agent based on the total weight of the compressed core;
       (iii) a water soluble pharmaceutically acceptable polymer binder;
       (iv) a conventional pharmaceutical excipient; and
    (b) a dual membrane coating around said core which consists essentially of:
       (i) an inner membrane of triacetin plasticized ethyl cellulose and hydroxypropyl cellulose; and
       (ii) an outer membrane of pseudoephedrine, terfenadine and hydroxypropyl cellulose.

* * * * *